(12) United States Patent
Siedenburg

(10) Patent No.: US 11,413,005 B2
(45) Date of Patent: Aug. 16, 2022

(54) CONSTITUTIVE EQUATION FOR NON-INVASIVE BLOOD PRESSURE MEASUREMENT SYSTEMS AND METHODS

(71) Applicant: Stryker Corporation, Kalamazoo, MI (US)

(72) Inventor: Clinton T. Siedenburg, Everett, WA (US)

(73) Assignee: Stryker Corporation, Kalamazoo, MI (US)

(*) Notice: Subject to any disclaimer, the term of this patent is extended or adjusted under 35 U.S.C. 154(b) by 477 days.

(21) Appl. No.: 16/103,797

(22) Filed: Aug. 14, 2018

(65) Prior Publication Data

US 2019/0046152 A1 Feb. 14, 2019

Related U.S. Application Data

(60) Provisional application No. 62/545,433, filed on Aug. 14, 2017.

(51) Int. Cl.
*A61B 8/04* (2006.01)
*A61B 8/08* (2006.01)
*A61B 8/06* (2006.01)
*A61B 8/00* (2006.01)

(52) U.S. Cl.
CPC .............. *A61B 8/04* (2013.01); *A61B 8/0891* (2013.01); *A61B 8/5223* (2013.01); *A61B 8/06* (2013.01); *A61B 8/4236* (2013.01); *A61B 8/56* (2013.01)

(58) Field of Classification Search
CPC ....... A61B 8/04; A61B 8/0891; A61B 8/5223; A61B 8/06; A61B 8/56; A61B 8/4236
See application file for complete search history.

(56) References Cited

U.S. PATENT DOCUMENTS

| 4,336,808 | A | | 6/1982 | Ohno et al. |
| 5,249,577 | A | | 10/1993 | Shinomura et al. |
| 5,309,916 | A | * | 5/1994 | Hatschek ............... A61B 5/021 |
| | | | | 600/485 |
| 5,535,747 | A | | 7/1996 | Katakura |
| 6,176,832 | B1 | | 1/2001 | Habu et al. |

(Continued)

FOREIGN PATENT DOCUMENTS

| EP | 0898938 A2 | 3/1999 | |
| WO | WO-2008050334 A2 * | 5/2008 | ......... G01S 7/52087 |

(Continued)

OTHER PUBLICATIONS

Beulen et al. "Toward Noninvasive Blood Pressure Assessment in Arteries by Using Ultrasound", Ultrasound in Med. & Biol., vol. 37, No. 5, pp. 788-797, 2011.

(Continued)

*Primary Examiner* — Bill Thomson
*Assistant Examiner* — Zainab Mohammed Aldarraji
(74) *Attorney, Agent, or Firm* — Lee & Hayes, P.C.

(57) ABSTRACT

The disclosed devices, systems and methods measure non-invasive blood pressure in a patient. Energy emissions, such as ultrasound or light, are emitted into tissues of the patient. The emitted energy reflects from various tissues, such as flowing blood and vessels, and can be detected, or received, to generate a reflected energy signal or data. The reflected energy can be processed, such as by using a constitutive equation, to calculate the blood pressure.

23 Claims, 3 Drawing Sheets

(56) References Cited

U.S. PATENT DOCUMENTS

| | | | |
|---|---|---|---|
| 6,261,233 B1 | 7/2001 | Kantorovich | |
| 6,419,632 B1 | 7/2002 | Shiki et al. | |
| 6,676,600 B1 | 1/2004 | Conero et al. | |
| 7,125,383 B2* | 10/2006 | Hoctor | A61B 8/04 600/438 |
| 7,306,563 B2 | 12/2007 | Huang | |
| 7,621,876 B2* | 11/2009 | Hoctor | A61B 5/02125 600/437 |
| 7,815,574 B2* | 10/2010 | Mourad | A61B 8/485 600/453 |
| 8,738,128 B2 | 5/2014 | Pearce et al. | |
| 9,161,701 B2* | 10/2015 | Lading | A61B 5/02125 |
| 10,722,209 B2* | 7/2020 | Chen | A61B 8/085 |
| 2002/0177781 A1* | 11/2002 | Amano | A61B 5/02108 600/485 |
| 2005/0131282 A1 | 6/2005 | Brodnick et al. | |
| 2005/0143640 A1* | 6/2005 | Hoctor | A61B 8/04 600/407 |
| 2006/0211942 A1* | 9/2006 | Hoctor | A61B 8/4236 600/438 |
| 2007/0093702 A1* | 4/2007 | Yu | A61B 5/0051 600/326 |
| 2007/0167844 A1* | 7/2007 | Asada | A61B 5/6826 600/485 |
| 2011/0040197 A1 | 2/2011 | Welch et al. | |
| 2012/0123246 A1 | 5/2012 | King et al. | |
| 2014/0143064 A1 | 5/2014 | Tran | |
| 2014/0200423 A1 | 7/2014 | Eisen et al. | |
| 2015/0073230 A1* | 3/2015 | Stergiou | A61B 5/02125 600/301 |
| 2015/0238095 A1 | 8/2015 | Lading et al. | |
| 2015/0327785 A1* | 11/2015 | Lading | A61B 5/726 600/438 |
| 2015/0327786 A1* | 11/2015 | Lading | A61B 5/1126 600/437 |
| 2016/0030758 A1 | 2/2016 | Guiney et al. | |
| 2016/0038117 A1* | 2/2016 | Tamada | A61B 8/4236 600/438 |
| 2016/0095572 A1 | 4/2016 | Aguren | |
| 2016/0262639 A1* | 9/2016 | Ukawa | A61B 5/02116 |
| 2016/0287095 A1 | 10/2016 | Gu | |
| 2016/0345930 A1* | 12/2016 | Mizukami | A61B 8/02 |
| 2017/0000688 A1 | 1/2017 | Kaufman et al. | |
| 2017/0042504 A1* | 2/2017 | Rich | A61B 8/04 |
| 2017/0172429 A1* | 6/2017 | Takoh | A61B 5/02225 |
| 2017/0273664 A1 | 9/2017 | Baym et al. | |
| 2017/0360313 A1* | 12/2017 | Baek | A61B 5/02108 |
| 2018/0078155 A1* | 3/2018 | Baek | G16H 50/50 |
| 2018/0110667 A1 | 4/2018 | Freeman et al. | |
| 2018/0199834 A1* | 7/2018 | Siedenburg | A61B 8/04 |
| 2018/0224534 A1 | 8/2018 | Schulte | |
| 2018/0235567 A1* | 8/2018 | Bezemer | A61B 8/42 |
| 2018/0369065 A1* | 12/2018 | Siedenburg | A61B 5/0205 |
| 2019/0053779 A1 | 2/2019 | Siedenburg | |
| 2019/0125191 A1* | 5/2019 | Siedenburg | A61B 5/022 |

FOREIGN PATENT DOCUMENTS

| | | | |
|---|---|---|---|
| WO | WO2016081517 A2 | 5/2016 | |
| WO | WO-2017032648 A1 * | 3/2017 | A61B 5/02007 |

OTHER PUBLICATIONS

European Office Action dated Jan. 12, 2021 for European patent application No. 18703419.4, a counterpart foreign application of U.S. Appl. No. 15/874,796, 5 pages.

International Search Report & Written Opinion, dated Jan. 25, 2018; International Application No. PCT/US2017/60708, filed Nov. 8, 2017; 9 pages.

International Search Report & Written Opinion, dated Apr. 17, 2018; International Application No. PCT/US2018/014273, filed Jan. 18, 2018; pp. 1-14.

Murgo et al. "Aortic Input Impedance in Normal Man: Relationship to Pressure Wave Forms", American Heart Association, 1980, pp. 105-116.

O'Rourke, "Vascular Impedance in Studies of Arterial and Cardiac Function", School of Medicine, Univ. of New South Wales, St. Vincent's Hospital, Sydney, AU. pp. 571-623.

Office Action for U.S. Appl. No. 15/874,796, dated Jan. 28, 2021, Siedenburg, "Non-Invasive Blood Pressure Measurement Using Pulse Wave Velocity". 38 Pages.

Non Final Office Action dated Sep. 1, 2020 for U.S. Appl. No. 15/874,796, "Non-Invasive Blood Pressure Measurement Using Pulse Wave Velocity", Siedenburg, 48 pages.

Pereira et al., "Novel Methods for Pulse Wave Velocity Measurement", Physics Dept. Instrumentation Center, Univ. of Coimbra, Rua Larga, Coimbgra, PT. J. Med Biol. Eng. (2015) 555-565.

Soleimani et al. "Assessing the Blood Pressure Waveform of the Carotid Artery Using an Ultrasound Image Processing Method" Univ. of Tehran, IR, Ultrasonography 2017, pp. 144-152.

Struijk et al. "Blood Pressure Estimation in the Human Fetal Descending Aorta", Wiley InterScience, Ultrasound Obstet Gynecol 2008, pp. 673-681.

Tijsseling, et al., "Johannes von Kries and the History of Water Hammer", Journal of Hydraulic Engineering—ASCE, vol. 133, Jan. 2007, 9 pages.

Vennin et al., "Noninvasive calculation of the aortic blood pressure waveform from the flow velocity waveform: a proof of concept", AM J Physiol Heart Circ Physiol 309: H969-H976, 2015. First published Jul. 10, 2015.

U.S. Appl. No. 15/999,038, filed Aug. 16, 2018, titled "Non-invasive blood pressure measurement devices, systems and methods", 22 pages.

Bercoff, et al., "Supersonic Shear Imaging: A New Technique for Soft Tissue Elasticity Mapping," IEEE Transactions on Ultrasonics, Ferroelectrics, and Frequency Control, vol. 51, No. 4, Apr. 2004, pp. 396-409.

Bernal, et al., "Material Property Estimation for Tubes and Arteries Using Ultrasound Radiation Force and Anaiysis of Propagating Modes," Journal of the Acoustical Society of America, vol. 129(3), Mar. 2011, pp. 1344-1354.

Hoeks, et al., "Non-Invasive Measurement of Mechanical Properties of Arteries in Health and Disease", Proceedings of the Institution of Mechanical Engineers, Part H: Journal of Engineering in Medicine, Mar. 1999, vol. 213 Part H, pp. 195-202.

Jensen, J., "Comparison of Vector Velocity Imaging Using Directional Beamforming and Transverse Oscillation for a Convex Array Transducer," SPIE Medical Imaging, San Diego, CA, Feb. 2014, pp. 904012-1 to 904012-8.

Meinders, et al., "Simultaneous Assessment of Diameter and Pressure Waveforms in the Carotid Artery," Ultrasound in Medicine and Biology, vol. 30, No. 2, Feb. 2004, pp. 147-154.

Messas, et al., "Arterial Wall Elasticity: State of the Art and Future Prospects," Diagnostic and Interventional Imaging, Apr. 2013, pp. 561-569.

Montaldo, et al., "Ultrafast Compound Doppler Imaging: A New Approach of Doppler Flow Analysis," 2010 IEEE International Symposium on Biomedical Imaging: From Nano to Macro, Apr. 2010, pp. 324-327.

Office Action for U.S. Appl. No. 16/167,195, dated Feb. 1, 2021, Siedenburg, "Light-Based Non-Invasive Blood Pressure Systems and Method," 10 pages.

Office Action for U.S. Appl. No. 15/999,038, dated Mar. 25, 2021, Siedenburg, "Non-invasive blood pressure measurement devices, systems and methods," 27 pages.

Qi, et al., "Phase-Resolved Acoustic Radiation Force Optical Coherence Elastography," Journal of Biomedical Optics, vol. 17( 11), Nov. 2012, pp. 110505-1 to 110505-3.

Rabben, et al., "An Ultrasound-Based Method for Determining Pulse Wave Velocity in Superficial Arteries." Journal of Biomechanics, vol. 37, Oct. 2004, pp. 1615-1622.

Rajan, et al., "Review of methodological developments in laser Doppler flowmetry," Lasers Med Sci, 24:269-283, Mar. 2009.

(56) References Cited

OTHER PUBLICATIONS

Office Action for U.S. Appl. No. 16/167,195, dated Jun. 4, 2021, "Light-Based Non-Invasive Blood Pressure Systems and Method", 12 Pages.
Bank, et al., "In Vivo Human Brachial Artery Elastic Mechanics Effects of Smooth Muscle Relaxation", Circulation Journal of hte American Heat Association,vol. 100( 1) , 199, pp. 41-47.
Office Action for U.S. Appl. No. 15/999,038, dated Sep. 30, 2021, Siedenburgh, "Non-Invasive Blood Pressure Measurement Devices, Systems and Methods", 44 pages.
Office Action for U.S. Appl. No. 15/999,038, dated Dec. 21, 2021, Siedenburg, "Non-Invasive Blood Pressure Measurement Devices, Systems and Methods", 42 pages.
Office Action for U.S. Appl. No. 16/167,195, dated Sep. 13, 2021, Siedenburg, "Light-Based Non-Invasive Blood Pressure Systems and Method", 13 pages.

* cited by examiner

CONSTITUTIVE EQUATION FOR NON-INVASIVE BLOOD PRESSURE MEASUREMENT SYSTEMS AND METHODS

CROSS-REFERENCE TO RELATED APPLICATIONS

This patent application claims the benefit of and priority to U.S. Provisional Patent Application Ser. No. 62/545,433, filed on Aug. 14, 2017, entitled "NIBP Using Ultrasound and a Constitutive Equation," the contents of all of these applications are hereby incorporated by reference in their entirety.

BACKGROUND

The blood pressure of a patient is a critical measurement that is used in monitoring and treating the patient. There are two means by which the blood pressure of the patient can be measured—one is invasive and the other is non-invasive. In the invasive means, the blood pressure is obtained by direct measurement, requiring a sensor to be inserted into the circulatory system of the patient to obtain the measurements. As such, the invasive means, while providing an accurate measurement, can cause discomfort in the patient or the subject for which the blood pressure is being measured. Additionally, there is an increased risk of complications and/or expense due to the invasive nature of such blood pressure measurement. Such increased complications risk and/or expenses can be unwarranted in many cases, such as during a simple patient examination.

In the non-invasive means, the sensing of the blood pressure is done externally to the patient. Typically, this involves the application of a cuff about a limb of the patient and the pressurization of the cuff to cut-off circulation through the limb. The pressure applied by the cuff to the limb is slowly reduced and as blood flow is resumed, the blood pressure can be measured based on the pressure remaining in the cuff. This process is often repeated multiple times to ensure an accurate measurement, with pauses required between measurement instances. While this means is non-invasive, it does require the temporary cessation of circulation in a portion of the patient, which can be damaging to the health of the patient and requires time for the process to be fully performed. Additionally, such non-invasive blood pressure measurement techniques are sensitive to motion of the patient and equipment, which can result in inaccurate and/or unobtainable blood pressure measurements. In patient transport or emergency situations, the patient and equipment can be subjected to a large amount of motion during time in which an accurate blood pressure measurement can be critical to assess the state of the patient.

Blood pressure measurement and/or monitoring can be improved by non-invasive blood pressure systems and/or methods that do not require the restriction of circulation and provides the accurate blood pressure values/measurements needed for patient treatment and/or monitoring.

DETAILED DESCRIPTION

Figure 1:
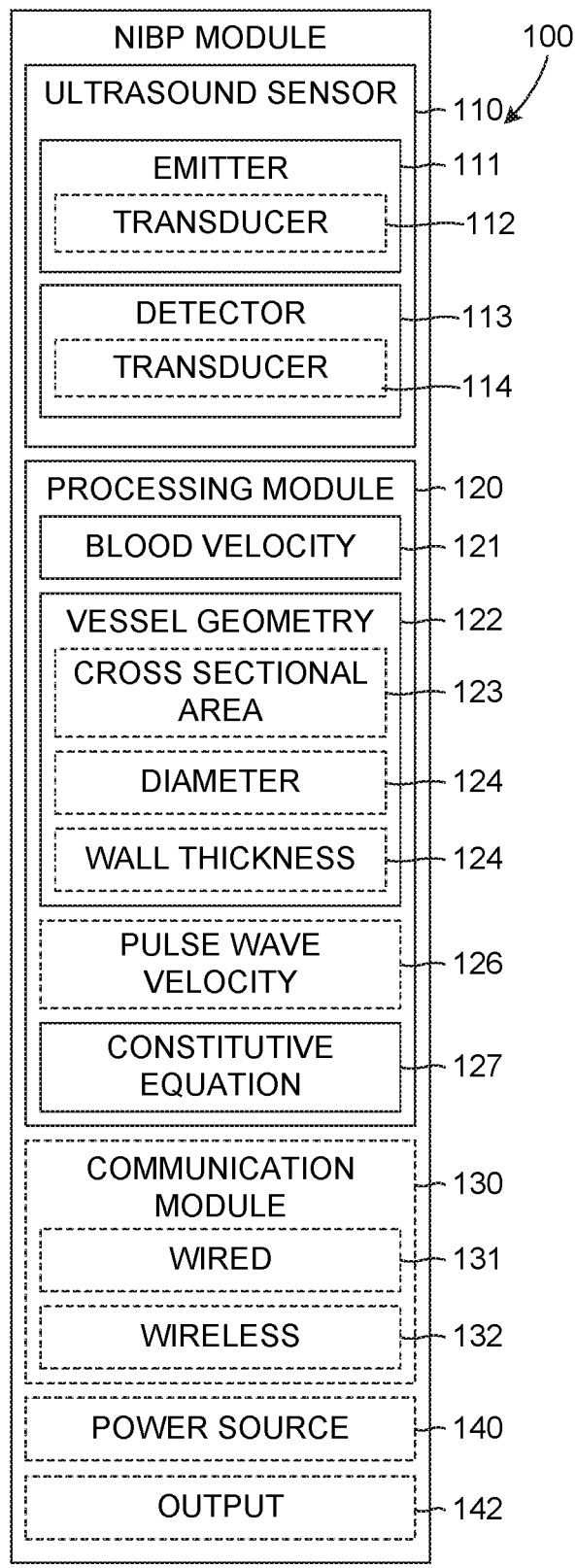
FIG. 1 illustrates an example non-invasive blood pressure (NIBP) module.

Devices, systems and method for measuring a non-invasive blood pressure in a patient are disclosed. Specifically, a constitutive equation for the non-invasive calculation/determination of a blood pressure without the use of a cuff, and non-invasive blood pressure measurement systems and methods using the constitutive equation, are described herein. Data and/or measurements of a patient's blood flow and vessel, or vascular, structures are obtained in a non-invasive manner and are used with the constitutive equation to calculate/determine a blood pressure of the patient. The requisite, or desired, blood flow and vessel structure measurements can be generated using a non-invasive blood pressure measurement device/system, such as those described herein. In an example, energy, such as light or ultrasound, are emitted into tissues and such energy reflects from blood flow and vessel structures within the tissues. The reflected energy can be received by a sensor or detector to cause a signal to be generated in response to the reception. The signal can be processed to determine various data/measurements, such as a velocity of a blood flow and one or more vessel geometry measurements, the values of which can be applied to the constitutive equation to calculate a blood pressure. The calculated/determined blood pressure can be used to provide blood pressure data to one or more devices, systems and/or users, such as for the treatment and/or monitoring of the patient.

Some conventional NIBP measurement systems rely on an initial calibration measurement, taken at least once, to convert a measured parameter that is correlated to a relative blood pressure value, such as pulse wave velocity, to an actual blood pressure value. The required calibration measurement is taken using a traditional blood pressure cuff, for example on the arm, the leg, or perhaps the finger of the patient. Such conventional, cuff-based NIBP measurement systems require an initial cuff-based calibration, and all calculations are based on a difference or differential value of that initial calibration measurement to achieve an actual blood pressure measurement.

The disclosed NIBP systems and devices instead take an instantaneous blood pressure measurement rather than a change from an initial, and distinct, calibration measurement. Avoiding the need for a calibration measurement prevents the patient from experiencing blood flow restriction altogether. Interrupting the blood flow requires that the patient's appendage being measured is compressed to restrict the blood flow. Such restriction of the patient's blood flow prevents such conventional methods of measuring blood pressure from being applied to areas of the patient's body that cannot withstand restricted blood flow, such as a patient's neck or internal organs, for example. In short, the disclosed embodiments are self-calibrating NIBP systems and methods that do not temporarily interrupt the flow of blood.

The ability of the disclosed self-calibrating NIBP technology to avoid a vessel restriction calibration step is from the use of the constitutive equation, described below. The constitutive equation relates three terms, an initial pressure, an elasticity of the vessel being interrogated and a resistance in the vessel due to viscosity. A useful constitutive equation may simply relate pressure to elasticity of the vessel. These terms can be expressed using measurable values, such as those obtained using the disclosed NIBP system(s)/process(es), and various assumptions/simplifications, which allows for the use of the constitutive equation in the calculation/determination of a blood pressure.

One of the measurable values can include a vessel geometry that can be acquired using light and/or ultrasound as a time varying waveform. Additionally, other measurable values, such as blood velocity can be similarly acquired. The time-varying nature of the blood velocity and/or vessel geometry means that these values can be measured at a much finer resolution than a cardiac cycle. That is to say that the time-varying values can be measured continuously during the cardiac cycle for as many cardiac cycles as is desired. With this disclosure, blood pressure can be monitored continuously throughout the cardiac cycle with as fine a resolution as is required, and this can be done for as many contiguous cardiac cycles as is desired for beat-to-beat monitoring, or as intermittently as desired.

Another variable that can be measured is a pulse wave velocity (PWV) of the patient. The PWV measurement can be used with one or more of the blood velocity and/or vessel geometry measurements to calculate a blood pressure of a patient. Additionally, the PWV measurement can be used in the constitutive equation, as described below.

FIG. 1 illustrates an example non-invasive blood pressure (NIBP) module 100 that includes an ultrasound sensor 110, a processing module 120, and, optionally, a communication module 130 and/or power source 140. The NIBP module 100 can be placed on a patient to emit ultrasound into the tissues of the patient, the reflections of which are then received by the NIBP module 100. By processing the received reflected energy, the NIBP module 100 can calculate/determine the blood pressure of the patient in a non-invasive manner. Further, this blood pressure measurement can be an instantaneous, or beat-to-beat, measurement, which can provide for the enhanced, or improved, monitoring of patients and their physiological condition, similar to the monitoring that may be achieved using an invasive method.

The ultrasound sensor 110 can include an emitter 111 and detector 113. The emitter 111 can include one or more transducers 112 to generate/emit the ultrasonic energy that is transmitted into the tissues of the patient. In an example, multiple transducers 112 can be contained within the emitter 111 and can be arranged, such as in a linear array arrangement, to emit ultrasonic energy. Ultrasonic energy can be emitted from the emitter 111 as a single beam, or multiple beams, that are generated by the one or more transducers 112. The emitted ultrasonic energy passes through the tissues of the patient and reflects from various structures/features therein, such as blood flowing through a vessel and/or the blood vessel wall. Energy reflected from moving tissues, such as flowing blood and/or expansion/contraction of the vessel wall(s), exhibits a Doppler shift indicative of the velocity, or speed, or rate of change of phase over time, of the motion. The reflected energy can be received by the detector 113 of the NIBP module 100 to generate a signal indicative of the tissues and/or motion therein. In FIG. 1, the emitter 111 and the detector 113 are shown with respective transducers 112, 114, each representative of either a single transducer or multiple transducers, such as an array configuration. Any combination of transducers can be used. In some applications, such as ultrasound, the emitter 111 and detector 113 use the same, single transducer or the same set of multiple transducers (not shown in FIG. 1). Regardless of the energy type, the detected reflection of the emitted energy is converted to an electrical signal—the reflected energy signal—by one or more transducers.

In another example, the NIBP module 100 can emit light energy into the patient tissues instead of or, or in addition to, ultrasonic energy, to generate the reflected energy signal. The emitted light can be in a visible or non-visible spectrum and can include a specified, or varying, wavelength(s) and/or frequency(s). The signal generated by the reception of the reflected light energy, a reflected energy signal, can be processed to determine various data/measurements regarding the patient tissues, such as features and/or motion thereof.

The signal generated in response to the received reflected ultrasonic energy can be processed by the processing module 120 to determine/calculate various data contained therein, such as the blood velocity 121, a vessel geometry 122, and/or, optionally, pulse wave velocity (PWV) 126. Using the data, the processing module 120 can determine a blood pressure using a constitutive equation 127 contained therein and explained below.

To measure the blood velocity 121, the ultrasound sensor 110 can be operated in a Doppler mode, such as a pulse wave Doppler (PWD) mode, to capture Doppler information of the blood flowing through a vessel. Alternatively, or additionally, other ultrasound operating modes/methods can be used to capture the Doppler information. Using this captured data, the processing module 120 can calculate/determine the blood velocity 121.

In an example in which a single ultrasound sensor 110 is used to obtain the data, the blood velocity 121 can be an average velocity of the blood flow within the vessel, or portion thereof, contained within a field of view of the ultrasound sensor 110. This averaging can be compensated for, if needed or desired, by correlating the average velocity measurement to a peak velocity measurement. The correlation can be analytically derived using beam profile data, such data regarding the assumed beam profile of the ultrasound sensor 110, with blood flow profile assumptions. Alternatively, the correlation can be empirically derived using data collected from a patient population. The empirically derived data can be contained/stored within the NIBP module 100 for recall and use in calculating/determining the blood velocity 121 from the received reflected ultrasound energy.

To measure vessel geometry 122, the ultrasound sensor 110 can be operated in a motion, or M-, mode to capture various states/dimensions of the vessel with respect to time. Using such captured data, various vessel geometry features, such as a cross-sectional area, inner, and/or outer, diameter and/or wall thickness, of the vessel can be calculated/determined. Alternatively, or additionally, other operating modes/methods of ultrasound can be used to capture the various vessel geometry measurements, such as A-mode, B-mode and/or other operating modes/methods such as plane wave imaging and shear wave imaging, for example.

The disclosed devices, methods, and systems measure vessel geometry 122 and can additionally and optionally measure blood velocity 121. Pulse wave velocity (PWV) 126 measurements/data can be optionally calculated/determined from the received reflected energy that includes the vessel geometr(ies) and optionally the blood velocity 121. Alternatively, the PWV 126 measurements can be received from another device/system external the NIBP module 100.

The various measurements are calculated/determined by the processing module 120 with respect to time, which allows the various measurements to be correlated with each other and applied to terms in the constitutive equation 127 that is used to determine a non-invasive blood pressure using such data. Using the calculated/determined data from the reflected ultrasonic energy, a corresponding blood pressure of the vessel can be calculated/determined. The calculated blood pressure data can be output from the NIBP module 100, such as by the communication module 130 and/or by an output, such as a display screen and/or speaker or any combination of these or other output options, included on the NIBP module 100.

In the example of FIG. 1, the processing module 120 is included with the NIBP module 100. However, in alternative embodiments, the processing module 120 can be external to the NIBP module 100 and can receive the obtained/acquired measurements and/or data from the NIBP module 100 for processing. The external, or remote, processing module 120 can receive data from the NIBP module 100, such as through a wired or wireless transmission, and can calculate/determine a non-invasive blood pressure from, or based on, the received data.

The optional communication module 130 can provide communication between the NIBP module 100 and an external device(s), or system(s), via a wired 131 and/or wireless 132 connection. In an example, the NIBP module 100 can be physically connected to another device/system using a wired connection 131 to transmit and/or receive data. In another example, the NIBP module 100 can transmit and/or receive data with an external device/system through wireless connection 132, such as through a network or local wireless connection 132. Example wireless connections 132 can include Wi-Fi, Bluetooth®, WiGig, and/or other wireless communication protocols/methods. Data transmitted from the NIBP module 100 can include the signal/data generated by, or indicative of, the received reflected ultrasound and/or light energy, measurement data, blood pressure data, operating data and/or other data regarding the NIBP module 100. Data received by the NIBP module 100 can include data/measurements obtained from processing the reflected energy signal, operating instructions and/or other data.

The NIBP module 100 can also include an optional power source 140 that can provide the necessary energy for the various functions and/or features of the NIBP module 100. The power source 140 can be fixed, removable and/or replaceable and can be optionally rechargeable from an external power source. Alternatively, the power source 140 can include a connection that physically, or wirelessly, couples the NIBP module 100 to an external power source to provide the requisite, or desired, power for the various functions/features of the NIBP module 100. Wireless coupling to an external power source can include an inductive power coupling to supply power to the NIBP module 100. Alternatively, or additionally, the power source 140 can include energy harvesting capabilities, or technology, to harvest ambient energy from the environment about the NIBP module 100. Example energy harvesting can include harvesting of light, thermal, sonic, electromagnetic, and/or other ambient energy that can be used to provide electrical power to the NIBP module 100.

The NIBP module 100 can be integrated into one or more medical, or other, devices/systems, and/or coupled to it. Blood pressure, and/or other, data from the NIBP module 100 can be provided to the medical device/system, and/or a user, for patient treatment, patient monitoring and/or other purposes.

Figure 2:
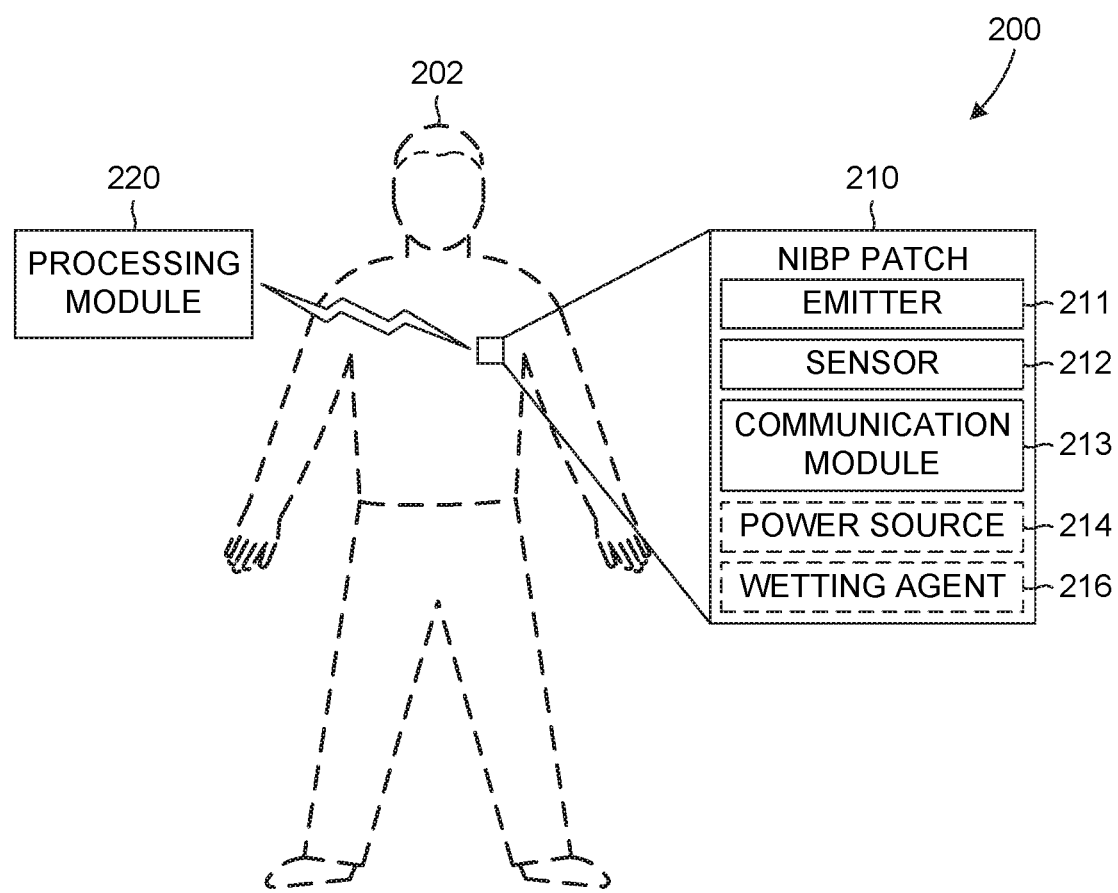
FIG. 2 illustrates an example non-invasive blood pressure system.

FIG. 2 illustrates an example non-invasive blood pressure system 200 that includes an NIBP patch 210 and an external processing module 220. The NIBP patch 210 can be placed on a patient 202 to generate a reflected energy signal/data that can be transmitted to the processing module 220 for processing, such as calculating/determining a blood pressure of the patient 202. The blood pressure data can be acquired and/or processed continuously and/or at intervals, such as at regular intervals, to generate blood pressure, or other, data.

The NIBP patch 210 can include an emitter 211 that emits energy, such as ultrasound or light, into the tissues of the patient 202. The energy reflected from the patient 202 tissues, such as reflected from moving blood and/or vessel structures, can be sensed by a sensor 212. In response to receiving the reflected energy, the sensor 212 can generate a reflected energy signal and/or data that can be transmitted from the NIBP patch 210 to the processing module 220 via the communication module 213. Communication between the communication module 213 of the NIBP patch 210 and the processing module 220 can be via a wired and/or a wireless connection that transmits the reflected energy signal and/or data, or a portion thereof. One or more, various communication protocols can be used to wireless transmit data between the NIBP patch 210 and the processing module 220. Example communication protocols can include Wi-Fi, Bluetooth, WiGig, and/or other wireless communication protocols/methods.

A power source 214 can be included in/on the NIBP patch 210 to provide the requisite, or desired, power to the various functions and/or features of the NIBP patch 210. The power source 214 can be permanently coupled or removable/replaceable from the NIBP patch 210. Additionally, the power source 214 can be optionally rechargeable to allow for reuse and/or extended use of the power source 214. In another embodiment, the power source 214 can include energy capture capabilities to collect, or harvest, power from external sources to provide power to the various functions and/or features of the NIBP patch 210. Example energy harvesting can include the harvest of light, thermal, sonic, electromagnetic, and/or other ambient energy to provide electrical power to the various functions and/or features of the NIBP patch 210.

In an embodiment in which the emitter emits ultrasonic energy into the tissues of the patient 202, the NIBP patch 210 can include a wetting agent 216 to facilitate the transmission of the ultrasonic energy into the patient 202 tissues and to couple the sensor 212 to the patient's body to receive the ultrasonic reflection from the patient tissues. The NIBP patch 210 can have a self-dispensing wetting agent that is applied to the patch and/or the patient before, while, or after the patch is placed on, or applied. For example, placing the NIBP patch 210 on the patient, or as part of such action, can cause the wetting agent 216 to be released beneath the emitter 211 to assist with transmission of the emitted energy into the tissues of the patient 202. Alternatively, a user can separately apply the wetting agent to the patch and/or patient before the emission of energy begins.

The processing module 220 receives the reflected energy signal and/or data from the NIBP patch 210 and determines various data and/or measurements regarding blood flow and/or vessel structures of the patient 202. Blood velocity, vessel geometry and/or pulse wave velocity (PWV) of the patient 202 can be calculated/determined by the processing module 220. The processing module 220 can use this data, or portions thereof, to calculate/determine a blood pressure of the patient 202, such as by utilizing the constitutive equation described below. The calculated/determined blood pressure data can be provided to a user and/or an external device/system by the processing module 220. Such blood pressure data can be used in, or assist with, monitoring and/or treatment of the patient 202.

Figure 3:
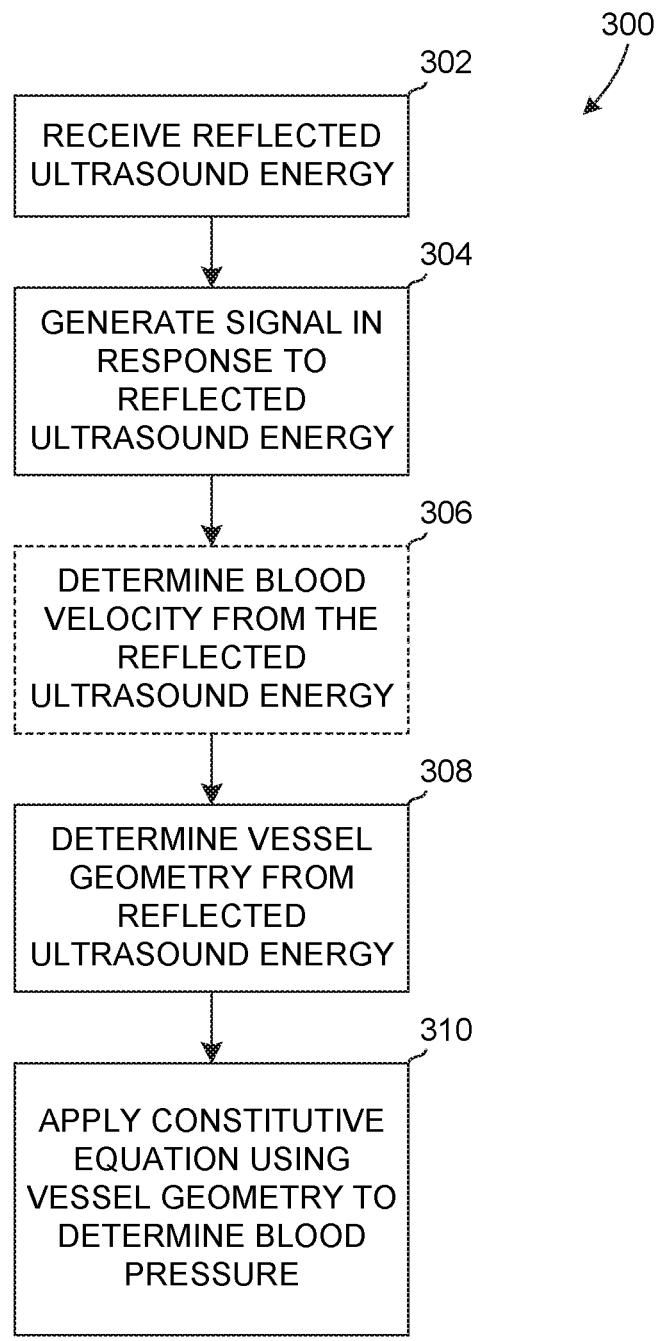
FIG. 3 illustrates an example non-invasive blood pressure method.

FIG. 3 illustrates an example non-invasive blood pressure method 300 by which a blood pressure can be calculated/determined non-invasively using one or more of systems/processes, such as those described herein. The method 300 allows data/measurements regarding blood flow and vessel structures to be obtained in a non-invasive manner and to use such data/measurements to calculate/determine a blood pressure of a patient.

At 302 reflected ultrasound energy is received. Ultrasound energy can be previously transmitted, or emitted, into tissues of a patient and some portion of the emitted energy reflects from the various tissues and/or structures that the emitted ultrasound energy contacts. This reflected ultrasound energy is received at 302 and is representative/indicative of the various tissues and/or structures that the emitted ultrasound energy contacts during transmission through the tissues. In another embodiment, other energy, such as light energy, can be transmitted/emitted into the tissues to generate reflected energy.

At 304, a signal is generated in response to the received ultrasound energy. The generated signal is indicative of the various tissues from which the transmitted ultrasound energy is reflected, such as a blood vessel and/or flowing blood. This signal can be processed, such as at 306, to determine, or calculate, a blood velocity. Flowing blood, or moving vessel structures, cause the reflected energy to exhibit a Doppler shift that can be used to determine the velocity, or speed, of the flowing blood or moving structure. Additionally, the signal can be processed, such as at 308, to determine, or calculate, vessel geometry. The vessel geometry can include various measurements regarding the vessel, such as an inner diameter, cross-sectional area, wall thickness and/or various other dimensional measurements of the blood vessel. The measurements/calculations of 306 and 308 can be made with respect to time so that one or more data points for each can be collected and/or correlated.

At 310, the values of the blood velocity and vessel geometry measurements can be applied to a constitutive equation, such as described below, to determine a blood pressure. Since these measurements can be made with respect to time, the blood pressure calculation/determination can be similarly made.

Described and shown below is a constitutive equation that can be used to calculate a pressure using measured and/or assumed data/terms as outlined below:

$$P = P_0 + \beta(x)\frac{\sqrt{A(x,t)} - \sqrt{A_0(x)}}{A_0(x)} + \frac{\Gamma(x)}{A_0(x)\sqrt{A(x,t)}}\frac{\delta A(x,t)}{\delta t} \quad \text{(Equation 1)}$$

Equation 1 is based upon the Voigt model and Laplace's Law. Other forms of a constitutive equation arise from using other models such as the Maxwell model, the Kelvin model, the Boltzmann model, and many others, all of which are included in this disclosure. The Laplace's Law used in Equation 1 relates stress on the surface of a volume to the pressure across the surface. The Voigt model used in Equation 1 is an example that relates tensile stress of the blood vessel to the strain using Young's modulus and viscosity. The combination of Laplace's Law and the Voigt model is used to derive Equation 1.

Equation 1 is a model of arterial mechanics that relates a pressure (P) of the vessel to three main terms. The first term is an initial pressure ($P_0$) of the vessel. The second term is comprised of a vessel elasticity factor, ($\beta(x)$, an initial cross-sectional area ($A_0$) of the vessel, and a cross-sectional area of the vessel at time t (A(x,t)). The third term describes a resistance of flow and is comprised of a resistance factor, $\Gamma(x)$, due to a viscosity of the flowing fluid, such as blood, an initial cross-sectional area ($A_0$) of the vessel, a cross-sectional area of the vessel at time t (A(x,t)), as well as its rate of change. Therefore, the pressure P of a vessel can be calculated based on the above-described terms, which are further described below.

$$\beta(x) = 3/3\sqrt{\pi E}(x)h(x) \quad \text{(Equation 2)}$$

Equation 2 is part of the second term of Equation 1, which describes the elasticity of the vessel and includes the Young's modulus (E(x)) and a wall thickness (h(x)) of the vessel. The Young's modulus of the vessel can be calculated/determined, as further described below, or can be an estimated and/or empirically derived value that can be applied to the vessel, such as in a particular/specific or a general fashion. It may also be derived from other related mechanical properties and assumptions.

$$\Gamma(x) = 2/3\sqrt{\pi}\varphi(x)h(x) \quad \text{(Equation 3)}$$

Equation 3 is part of the third term of Equation 1, which describes the resistance to flow through the vessel. Equation 3 includes terms for the wall viscosity ($\varphi(x)$) and the wall thickness h(x) of the vessel.

Measurable values of the constitutive equation—Equation 1—and the terms of Equation 1—Equations 2 and 3—include the vessel cross-sectional area A(x) and wall thickness h(x). Other values, such as the initial cross-sectional area $A_0(x)$, Young's modulus E(x) and wall viscosity $\varphi(x)$, can be calculated/determined based on vessel measurements and/or derived from empirical data, and/or an assumed value, or derived from other related mechanical properties, to allow for calculating the pressure P of a vessel/patient, using measurement data collected in the disclosed non-invasive manner.

The first term of Equation 1, the initial pressure $P_0$, can be expressed as a function of the initial cross-sectional area of the vessel $A_0(x)$. That is, when $P_0 = 0$ the cross-sectional area of the vessel is at an initial state $A_0(x)$. At the state where $P_0 = 0$, the initial cross-sectional area of the vessel, $A_0(x)$, is likely not zero, but is some magnitude, or fraction, of the cross-sectional area of the vessel at the end of diastole, $A_d(x)$, which is a measurable value, such as by an ultrasound, light-based or other non-invasive method. Setting the initial pressure $P_0$ to zero allows the first term of the constitutive equation, Equation 1, to be cancelled and allows the initial cross-sectional area value $A_0(x)$ to be expressed as a magnitude of the measured cross-sectional area of the vessel at the end of diastole $A_d(x)$, as shown below in Equation 4.

$$A_0(x) = \gamma A_d(x) \quad \text{(Equation 4)}$$

Using this, the constitutive equation, Equation 1, can be simplified and rewritten as Equation 5, below:

$$P = \beta(x)\frac{\sqrt{A(x,t)} - \sqrt{\gamma A_d(x)}}{\gamma A_d(x)} + \frac{\Gamma(x)}{\gamma A_d(x)\sqrt{A(x,t)}}\frac{\delta A(x,t)}{\delta t} \quad \text{(Equation 5)}$$

In Equation 5, the initial cross-sectional area of the vessel $A_0$ is now expressed at a magnitude $\gamma$, or fraction, of the cross-sectional area of the vessel during the diastole phase of the cardiac cycle, $A_d$, which is a measurable variable, such as by using an ultrasound, light-based, or other non-invasive system/method.

In another, or alternative, arrangement of the terms, the water hammer equation can be used to express pressure (P) as a function of the density (p), pulse wave velocity (PWV), and flow (U). The water hammer equation can be applied/used to solve for the pressure P at the end of the diastole phase/beginning of systole phase where reflective waves of the vessel have expired. The water hammer equation assumes a zero flow condition corresponds to zero pressure. The cross-sectional area of the vessel at end diastole, $A_d$, and the flow $U_d$ at end diastole and PWV values are measurable parameters/values that can be taken/made using a non-invasive system/method. At this state, the water hammer equation can be expressed as Equation 6 as shown below:

$$P_d = \rho PWV U_d \qquad \text{(Equation 6)}$$

Equation 6 can then be applied to the constitutive equation, Equation 1, in place of the term $P_0$, allowing the constitutive equation to be expressed as Equation 7, shown below:

$$P = \rho PWV U_d + \beta(x) \frac{\sqrt{A(x,t)} - \sqrt{A_d(x)}}{A_d(x)} + \frac{\Gamma(x)}{A_d(x)\sqrt{A(x,t)}} \frac{\delta A(x,t)}{\delta t} \qquad \text{(Equation 7)}$$

Equation 6 contains the term PWV, which can be a measured or calculated value. To calculate PWV, the water hammer-based equation, Equation 6, can written in a differential form, Equation 8, and applied from the end of the diastole phase to peak systole phase, Equations 9 and 10, shown below:

$$dP = \rho PWV dU \qquad \text{(Equation 8)}$$

$$\Delta P = P_s - P_d \qquad \text{(Equation 9)}$$

$$\Delta U = U_s - U_d \qquad \text{(Equation 10)}$$

Using Equations 7-10, the PWV term can be calculated/expressed as shown in Equation 11 below:

$$PWV = \frac{1}{\rho \Delta U} + \left\{ \beta(x) \frac{\sqrt{A_s(x,t)} - \sqrt{A_d(x)}}{A_d(x)} + \frac{\Gamma(x)}{A_d(x)} \left( \frac{1}{\sqrt{A_s(x,t)}} \frac{\delta A_s(x,t)}{\delta t} - \frac{1}{\sqrt{A_s(x,t)}} \frac{\delta A_d(x,t)}{\delta t} \right) \right\} \qquad \text{(Equation 11)}$$

Approximating Equation 11 by neglecting the viscosity term $\Gamma(x)$ (the second term) and substituting the definition for $\beta$ of Equation 2 as well as Young's Modulus in terms of PWV from the definition of PWV from Equation 12 below, it can be shown that assuming that $R_0$ of equation 12 is approximated by the average of the peak systole and diastole geometries:

$$PWV = \frac{3}{4} \Delta U \frac{A_d(x)}{A_s(x,t) - A_d(x)} \qquad \text{(Equation 11A)}$$

Using Equation 11A, PWV can be calculated, using the various measured terms above, at a single location, rather than across/between two locations, as might be typically done. Alternatively, the PWV can also be a measured value that is obtained, or measured, in a non-invasive manner.

Looking further at the water hammer-based equation, Equation 6, there is an implicit assumption that both pressure, Pa, and blood flow, $U_d$, approach zero together since density (φ remains constant and PWV is a scalar of the blood vessel to equate the flow to a corresponding pressure. This assumption holds true in practice, since a decrease in either pressure or blood flow in a real-world vessel, or vascular, system results in a decrease in the other of the pressure or blood flow. The vascular pressure approaches zero when the heart stops pumping resulting in the blood not flowing.

The second term of the constitutive equation, Equation 1, models the effects of the elasticity of the vessel. Using an ultrasound, light-based, or other non-invasive system/method, a diameter of the vessel can be measured with respect to time, which can be used to calculate the cross-sectional area of the vessel as a function of time. Further, as part of the vessel geometry, the vessel wall thickness, h(x), can be measured.

As part of the elasticity of the vessel, the Young's modulus of the vessel is considered, as shown in Equation 2. An estimate of the Young's modulus of the vessel can be estimated/calculated using the Moens-Korteweg equation, Equation 12 below:

$$PWV = \sqrt{\frac{E(x)h(x)}{2R_0(x)\rho}} \qquad \text{(Equation 12)}$$

As shown in Equation 12, by using a pulse wave velocity (PWV) measurement, the Young's modulus E(x) can be estimated/calculated. The other terms of Equation 12 are measurable values, such as the vessel wall thickness h(x) and the vessel radius $R_0(x)$, which can be obtained by non-invasive systems/methods. The density of the blood p is also a known value. Using these measured and known values, the Young's modulus can be obtained for use in the constitutive equation.

Equation 2 also includes a coefficient, or scalar, of 3 that accounts for the effects of viscosity. This coefficient is an estimate and may be adjusted over time to better account for the effects of viscosity and it can be a static or dynamic value depending on the available data. To better estimate the coefficient, measured data and regression techniques can be used to refine the estimate to a more accurate value.

The third term of the constitutive equation, Equation 1, represents the viscosity effects. The third term includes a partial derivative of the cross-sectional area of the vessel $$\frac{\delta A(x,t)}{\delta t},$$

with respect to time, which can be calculated/determined from the vessel diameter being measured with respect to time, such as by a non-invasive system/method.

The third term of Equation 1 includes Equation 3, which includes a wall thickness factor h(x) that can be measured. Another factor of Equation 3 is the wall viscosity φ(x) of the vessel. The wall viscosity value can be an estimated, or assumed, value that can be specific to the vessel being measured. The estimate of the value can be obtained/determined using regression techniques and previously measured values. Additionally, a look-up table for various vessels/vessel properties correlated to wall viscosity values can be generated and used in the calculation of Equation 3.

The simplest constitutive equation can be determined by assuming $P_0$ is essentially zero and neglecting viscosity, which transforms Equation 1 above into the following simplified Equation 13 based on these assumptions:

$$P \approx \beta(x) \frac{\sqrt{A(x,t)} - \sqrt{A_0(x)}}{A_0(x)} \quad \text{(Equation 13)}$$

Substituting in the definition of β from Equation 2 and assuming that the radius as a function of time can be written as a change from the base value, blood pressure can be determined as:

$$P \approx \frac{4}{3} \frac{E(x)h(x)}{R_0^2(x)} \Delta R(x,t) \quad \text{(Equation 14)}$$

Equation 14 indicates that the pressure waveform is approximately a scaled version of the waveform for the change in radius or distension. One could, therefore, write that pressure as a function of time is:

$$P(x,t) \approx \alpha \Delta R(x,t) \quad \text{(Equation 15)}$$

The scale factor, α, of Equation 15 could be determined a variety of ways. First, the scale factor, α, could be directly determined as in Equation 14 by measuring wall thickness, vessel radius, and Young's modulus. Young's modulus can be determined in a number of ways including from the measurement of PWV and density or some combination of other mechanical properties such as bulk modulus, Poison's ratio, Lame parameters, P-wave and S-wave velocities, etc. or by some lookup table.

Second, scale factor, α, could be computed by finding the scale factor, α, that when applied to a normalized distension curve (scaled by the peak so the maximum value is unity), it aligns at a known value of pressure at a particular point in time. For example, the peak distension occurs at the same time the peak pressure and peak blood velocity occurs which is at peak systole. The scale factor α, then, is the pressure at peak systole as computed by the water hammer equation using estimates of the velocity of the blood flow at peak systole, the PWV, and the blood density.

The scale factor, a can also be calculated a third way that uses an empirical approach using tabulated statistical values by vessel and vessel health to make the conversion from distension to pressure. Using the above-described equations, estimations and/or assumptions, non-invasive systems/methods, such as ultrasound, light-based, or other systems/methods, can be used to determine/calculate the blood pressure of a patient. The benefit of the disclosed blood pressure determination/calculation is that the measurements are with respect to time, which allows instantaneous blood pressure measurements to be obtained using non-invasive methods.

It should also be noted that the absolute value of the vessel geometry can be estimated for zero pressure and zero blood flow. Since the water hammer equation of Equation 8 represents a linear relationship between pressure and blood flow, and since Equation 15 represents a linear relationship between pressure and vessel geometry (such as radius or square root of area), then there is a linear relationship between blood flow and vessel geometry. Since blood flow measurements at systole and diastole can be easily made along with the vessel geometries, complete information corresponding to this straight line ($R = mU + R_0$) can be determined from these two pairs of measured points ($R_s$, $U_s$) and ($R_d$, $U_d$). That is, the slope (m) and intercept ($R_0$) of this line can be computed with these two measurement sets. Thus, in Equation 1, the $A_0$ that corresponds to $P_0$ can be known absolutely when $P_0 = 0$, thus more fully characterizing the elastic performance of the vessel. Therefore, pressure then can be related to absolute radius and not just the change in radius as is done in Equation 15.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A medical system, comprising:
a single ultrasound sensor comprising:
an emitter configured to emit a signal towards a single location of a blood vessel of a patient; and
a detector configured to receive a reflection of the signal from the single location of the blood vessel; and
a processor configured to:
determine, from the reflection of the signal, a geometry of the blood vessel at a first time and a geometry of the blood vessel at a second time;
determine a change between the geometry of the blood vessel at the first time and the geometry of the blood vessel at the second time;
determine a pulse wave velocity using the following equation:

$$PWV = \frac{3}{4} \Delta U \frac{A_d(x)}{A_s(x,t) - A_d(x)},$$

wherein PWV is the pulse wave velocity, $\Delta U$ is a change in flow of blood through the blood vessel between a diastole phase and a peak systole phase, $A_d(x)$ is a cross-sectional area of the blood vessel during the diastole phase, and $A_s(x,t)$ is the cross-sectional area of the blood vessel during the peak systole phase; and
determine a blood pressure of the blood vessel from the change between the geometry of the blood vessel at the first time and the geometry of the blood vessel at the second time and the pulse wave velocity.

2. The medical system of claim 1, wherein the signal comprises a single beam.

3. The medical system of claim 1, wherein the geometry of the blood vessel at the first time comprises an inner diameter, an outer diameter, a cross-sectional area, or a thickness of a wall of the blood vessel at the first time, and wherein the geometry of the blood vessel at the second time comprises an inner diameter, an outer diameter, a cross-sectional area, or a thickness of the wall of the blood vessel at the second time.

4. The medical system of claim 1, wherein the processor is further configured to determine
a velocity of blood flowing through the blood vessel.

5. The medical system of claim 1, further comprising a patch comprising the single ultrasound sensor and configured to be attached to the patient.

6. The medical system of claim 5, wherein the patch comprises a self-dispensing wetting agent, the patch being further configured to dispense at least a portion of the wetting agent on the patient when the patch is attached to the patient or as the patch is being attached to the patient.

7. The medical system of claim 5, wherein the patch is wirelessly coupled to the processor and further comprises a transceiver configured to transmit and receive data between the single ultrasound sensor and the processor, and
wherein the data transmitted between the single ultrasound sensor and the processor is indicative of the reflection of the signal.

8. The medical system of claim 1, wherein the single ultrasound sensor and the processor are integrated into a device.

9. The medical system of claim 8, wherein the device further comprises a transceiver configured to transmit and receive data between the device and a remote device.

10. The medical system of claim 9, wherein the data transmitted between the device and the remote device is indicative of the reflection of the signal, the geometry of the blood vessel at the first time, the geometry of the blood vessel at the second time, the change between the geometry of the blood vessel at the first time and the geometry of the blood vessel at the second time, or the blood pressure.

11. A method of measuring blood pressure in a patient without restricting a blood vessel of the patient, the method comprising:
emitting an ultrasound signal toward a single location of the blood vessel;
receiving a reflection of the ultrasound signal reflected from the single location of the blood vessel;
determining, from the reflection of the ultrasound signal, a geometry of the blood vessel at a first time;
determining, from the reflection of the ultrasound signal, a geometry of the blood vessel at a second time;
determining a change between the geometry of the blood vessel at the first time and the geometry of the blood vessel at the second time;
determining a pulse wave velocity using the following equation:

$$PWV = \frac{3}{4}\Delta U \frac{A_d(x)}{A_s(x,t) - A_d(x)},$$

wherein PWV is the pulse wave velocity, $\Delta U$ is a change in flow of blood through the blood vessel between a diastole phase and a peak systole phase, $A_d(x)$ is a cross-sectional area of the blood vessel during the diastole phase, and $A_s(x,t)$ is the cross-sectional area of the blood vessel during the peak systole phase; and
determining the blood pressure from change between the geometry of the blood vessel at the first time and the geometry of the blood vessel at the second time and the pulse wave velocity.

12. The method of claim 11, wherein the ultrasound signal comprises a single beam.

13. The method of claim 11, further comprising:
determining a velocity of blood flowing through the blood vessel.

14. The medical system of claim 1, wherein the processor is further configured to determine, from the reflection of the signal, a Young's modulus of the blood vessel.

15. The medical system of claim 14, wherein the blood pressure of the blood vessel is further determined from the Young's modulus.

16. The medical system of claim 14, wherein the geometry of the blood vessel at the first time comprises a wall thickness of the blood vessel at the first time; and
wherein blood pressure of the blood vessel is further determined using a constitutive equation comprising the pulse wave velocity, the Young's modulus, and the wall thickness of the blood vessel at the first time.

17. The method of claim 11, further comprising:
determining, from the reflection of the ultrasound signal, a Young's modulus of the blood vessel.

18. The method of claim 17, wherein the blood pressure of the blood vessel is further determined from the Young's modulus.

19. The method of claim 17, wherein the blood pressure of the blood vessel is further determined further comprising:
using a constitutive equation comprising the Young's modulus and the change between the geometry of the blood vessel at the first time and the geometry of the blood vessel at the second time, and the pulse wave velocity,
wherein, the geometry comprises a wall thickness of the blood vessel.

20. The medical system of claim 1, wherein the first time comprises the diastole phase and the second time comprises the peak systole phase.

21. The method of claim 11, wherein the first time comprises the diastole phase and the second time comprises the peak systole phase.

22. The method of claim 11, further comprising:
transmitting the geometry of the blood vessel at the first time, the geometry of the blood vessel at the second time, the change between the geometry of the blood vessel at the first time and the geometry of the blood vessel at the second time, or the blood pressure to a remote device.

23. The method of claim 11, wherein the geometry of the blood vessel at the first time comprises an inner diameter, an outer diameter, a cross-sectional area, or a thickness of a wall of the blood vessel at the first time, and
wherein the geometry of the blood vessel at the second time comprises an inner diameter, an outer diameter, a cross-sectional area, or a thickness of the wall of the blood vessel at the second time.

* * * * *